United States Patent [19]

Maugh et al.

[11] Patent Number: 5,149,657

[45] Date of Patent: * Sep. 22, 1992

[54] ESCHERICHIA COLI EXPRESSION VECTOR ENCODING BIOADHESIVE PRECURSOR PROTEIN ANALOGS COMPRISING THREE TO TWENTY REPEATS OF THE DECAPEPTIDE (ALA-LYS-PRO-SER-TYR-PRO-PRO-THR-TYR-LYS)

[75] Inventors: Kathy J. Maugh, Walnut, Calif.; David M. Anderson, Rockville, Md.

[73] Assignee: Enzon Labs Inc., Gaithersburg, Md.

[*] Notice: The portion of the term of this patent subsequent to Sep. 17, 2008 has been disclaimed.

[21] Appl. No.: 655,234

[22] Filed: Feb. 8, 1991

Related U.S. Application Data

[63] Continuation of Ser. No. 25,140, Mar. 12, 1987, which is a continuation-in-part of Ser. No. 671,967, Nov. 16, 1984, Pat. No. 4,798,791, and a continuation-in-part of Ser. No. 933,945, Nov. 24, 1986, abandoned, which is a continuation-in-part of Ser. No. 650,128, Sep. 13, 1984, abandoned.

[51] Int. Cl.$^5$ ............... C12N 15/00; C12N 1/21; C12N 15/70; C12N 15/62
[52] U.S. Cl. ............... 435/320.1; 435/252.33; 435/69.1; 435/69.7; 935/10; 935/60; 935/73; 530/353; 536/27
[58] Field of Search ............... 435/69.1, 69.7, 172.3, 435/252.33.3, 20.1; 536/27; 530/328, 324, 353; 935/23, 29, 73

[56] References Cited

U.S. PATENT DOCUMENTS

| | | | |
|---|---|---|---|
| 4,585,585 | 4/1986 | Waite | 530/328 |
| 4,687,740 | 8/1987 | Waite | 435/68.1 |
| 4,721,673 | 1/1988 | Uren et al. | 435/183 |
| 4,798,791 | 1/1989 | Anderson et al. | 435/69.1 |
| 5,049,504 | 9/1991 | Maugh et al. | 435/252.33 |

FOREIGN PATENT DOCUMENTS

| | | |
|---|---|---|
| 0035384 | 9/1981 | European Pat. Off. |
| 61-085400 | 4/1986 | Japan |
| 2162190 | 1/1986 | United Kingdom |

OTHER PUBLICATIONS

Waite, J. H., et al., *J. Biol. Chem.* 258:2911-2915 (1983).
Waite, J. H., In *Mollucsa*, vol. 1, pp. 467-504 (1983).
Waite, J. H. and Tanzer, M. L., *Science* 212:1038-1040 (1981).
Waite, J. H., et al., *Biochem.* 24:5010-5014 (1985).
Waite, J. H., *Biol. Rev.*, 58:209-231 (1983).
International Search Report for PCT/US/88/00876 (May 16, 1988).
Johnson, R., *Gen. Engin. News* Apr. 1985, pp. 14 and 18.
Waite, J. H., *J. Comp. Physiol. B* 156:491-496 (1986).
Doel, M. T. et al. 1980. *Nucleic Acids Res.* vol. 8 pp. 4575-4592.
Kempe, T. et al. 1985. *Gene* vol. 39 pp. 239-245.
Kramer, J. M. et al 1982. *Cell* vol. 30 pp. 599-606.
Itakura, et al., *Science*, vol. 198: pp. 1056-1063, (1977).
Marumo, et al., *Biochim. Biophys. Acta* 872: pp. 98-103, (1986).

*Primary Examiner*—Richard A. Schwartz
*Assistant Examiner*—Mary E. Mosher
*Attorney, Agent, or Firm*—Sterne, Kessler, Goldstein & Fox

[57] ABSTRACT

Recombinant production of a bioadhesive precursor protein analog comprising three, five, ten, fifteen or twenty repeated decapeptides of the formula Ala-Lys-Pro-Ser-Tyr-Pro-Pro-Thr-Tyr-Lys is disclosed.

2 Claims, 6 Drawing Sheets

FIG. 4

```
                      5                        10              15
        Met Ala Ala Ala Lys Pro Ser Tyr Pro Pro Thr Tyr Lys Ala Lys
        ATG GCG GCC GCG AAA CCA AGT TAC CCA CCG ACC TAC AAA GCG AAA
Cla 1       Not 1
                          20                    25              30
        Pro Ser Tyr Pro Pro Thr Tyr Lys Ala Lys Pro Ser Tyr Pro Pro
        CCA AGT TAC CCA CCG ACC TAC AAA GCG AAA CCG TCT TAC CCA CCG 35                        40              45
        Thr Tyr Lys Ala Lys Pro Ser Tyr Pro Pro Thr Tyr Lys Ala Lys
        ACC TAC AAA GCG AAA CCA AGT TAC CCA CCG ACC TAC AAA GCG AAA 50                    55              60
        Pro Ser Tyr Pro Pro Thr Tyr Lys Thr Pro Ala Ala Lys Pro Ser
        CCG TCT TAC CCA CCG ACC TAC AAA ACG CCG GCC GCG AAA CCA AGT
                                              Nae 1
                      65                        70              75
        Tyr Pro Pro Thr Tyr Lys Ala Lys Pro Ser Tyr Pro Pro Thr Tyr
        TAC CCA CCG ACC TAC AAA GCG AAA CCA AGT TAC CCA CCG ACC TAC 80                        85              90
        Lys Ala Lys Pro Ser Tyr Pro Pro Thr Tyr Lys Ala Lys Pro Ser
        AAA GCG AAA CCG TCT TAC CCA CCG ACC TAC AAA GCG AAA CCA AGT 95                       100             105
        Tyr Pro Pro Thr Tyr Lys Ala Lys Pro Ser Tyr Pro Pro Thr Tyr
        TAC CCA CCG ACC TAC AAA GCG AAA CCG TCT TAC CCA CCG ACC TAC

110
        Lys Thr Pro Ala Ser Met
        AAA ACG CCG GCA AGC ATG
                Nae 1    Sph 1
```

FIG. 5

```
                      5                        10                       15
  1 Ala Ala Ala Lys Pro Ser Tyr Pro Pro Thr Tyr Lys Ala Lys Pro
 16 Ser Tyr Pro Pro Thr Tyr Lys Ala Lys Pro Ser Tyr Pro Pro Thr
 31 Tyr Lys Ala Lys Pro Ser Tyr Pro Pro Thr Tyr Lys Ala Lys Pro
 46 Ser Tyr Pro Pro Thr Tyr Lys Thr Pro Ala Ala Lys Pro Ser Tyr
 61 Pro Pro Thr Tyr Lys Ala Lys Pro Ser Tyr Pro Pro Thr Tyr Lys
 76 Ala Lys Pro Ser Tyr Pro Pro Thr Tyr Lys Ala Lys Pro Ser Tyr
 91 Pro Pro Thr Tyr Lys Ala Lys Pro Ser Tyr Pro Pro Thr Tyr Lys
106 Thr Pro Ala Ala Lys Pro Ser Tyr Pro Pro Thr Tyr Lys Ala Lys
121 Pro Ser Tyr Pro Pro Thr Tyr Lys Ala Lys Pro Ser Tyr Pro Pro
136 Thr Tyr Lys Ala Lys Pro Ser Tyr Pro Pro Thr Tyr Lys Ala Lys
151 Pro Ser Tyr Pro Pro Thr Tyr Lys Thr Pro Ala Ala Lys Pro Ser
166 Tyr Pro Pro Thr Tyr Lys Ala Lys Pro Ser Tyr Pro Pro Thr Tyr
181 Lys Ala Lys Pro Ser Tyr Pro Pro Thr Tyr Lys Ala Lys Pro Ser
196 Tyr Pro Pro Thr Tyr Lys Ala Lys Pro Ser Tyr Pro Pro Thr Tyr
211 Lys Thr Pro Ala Ser Ser
```

ESCHERICHIA COLI EXPRESSION VECTOR ENCODING BIOADHESIVE PRECURSOR PROTEIN ANALOGS COMPRISING THREE TO TWENTY REPEATS OF THE DECAPEPTIDE (ALA-LYS-PRO-SER-TYR-PRO-PRO-THR-TYR-LYS)

The work described herein was performed with the aid of government funding, and the government has certain rights in the invention described and claimed below. Specifically, the work was supported by ONR Contract No. N00014-84-K-0290.

CROSS REFERENCE TO RELATED APPLICATIONS

This application is a continuation of application Ser. No. 07/025,140, filed Mar. 12, 1987 now abandoned, which is a continuation in part of U.S. Ser. No. 06/671,967, filed Nov. 16, 1984 now U.S. Pat. No. 4,798,791; and U.S. Ser. No. 06/933,945, filed Nov. 24, 1986, now abandoned, which is a continuation-in-part of U.S. Ser. No. 06/650,128, filed Sep. 13, 1984, now abandoned.

BACKGROUND OF THE INVENTION

1. Field of the Invention

The invention relates to the production in *Escherichia coli* of bioadhesive precursor proteins that can be converted to bioadhesives by enzymatic treatment. The bioadhesives so produced can be employed to bond substances in wet environments. Typically, the bioadhesives of the invention are employed as marine adhesives, biomedical adhesives or dental adhesives.

BRIEF DESCRIPTION OF BACKGROUND ART

The properties of adhesives generally must be tailored to meet the requirements of the particular environments in which they are to be used. Ideally, an adhesive should be cured and it should maintain both its adhesivity and cohesivity under the conditions of use. Curing is the altering of the physical properties of an adhesive by chemical or enzymatic means. In the case of the bioadhesives likely to result from the bioadhesive precursor proteins described herein, curing is likely to be due to the cross-linking of adjacent uncured adhesive molecules by catalytic and/or chemical agents. Curing may also involve adhesive cross-linking with the substrate.

Many adhesives that exhibit excellent adhesive properties under dry conditions suffer a substantial or total loss of those properties in wet environments. Furthermore, adhesives of the prior art cannot be cured in wet environments. Consequently, it has been particularly difficult to develop adhesives for use in wet environments, such as marine adhesives or adhesives for use in medical and dental applications.

Marine mussels and other sessile invertebrates have the ability to secrete adhesive substances by which they affix themselves to underwater objects. For example, mussels of the genus Mytilus, e.g., the species *Mytilus edulis* and *Mytilus californianus*, deposit an adhesive substance from the mussel foot that becomes cured, forming a permanent attachment to the substrate. A major component of the adhesive deposited by *M. edulis* has been identified as a hydroxylated protein of about 130,000 daltons (Waite, J. H., J. Biol. Chem., 258:2911-2915 (1983)). While this substance might make an excellent adhesive for use in wet environments, isolation of the uncured adhesive from mussels for commercial use is not practical since the extraction of 1 kg of the adhesive substance would be a labor-intensive process requiring about 5 to 10 million mussels.

Biochemical analysis of the *M. edulis* bioadhesive protein has shown it to be rich in lysine (20 residues/100) and hydroxylated amino acids (60 residues/100) (Waite, J. H., supra). At least a portion of the hydroxylated residues are 3,4-dihydroxyphenylalanine (DOPA) and hydroxyproline, formed by post-translational hydroxylation of tyrosine and proline residues, respectively. It is believed that post-translational hydroxylation, particularly of the tyrosine residues, is important in defining the adhesive properties of the protein (Waite, J. H., In Mollusca, Volume I, pp. 467-504 (1983); Pizzi, A., et al., *Ind. Eng. Chem. Prod. Res. Dev.*, 21:309-369 (1982) and Wake, W. C., "Adhesion and the Formulation of Adhesives", Applied Science Publish. Ltd. Barking, England (1982).

U.S. Pat. No. 4,585,585 describes a procedure for preparing a bioadhesive polymer by chemically linking decapeptide units produced by the enzymatic digestion of isolated mussel adhesive protein. In accordance with the disclosure of that patent, a bioadhesive protein is first isolated from phenol glands of mussels of the genus Mytilus using the protein purification procedures described by Waite and Tanzer in *Science*, 212:1038 (1981). The isolated bioadhesive, having a molecular weight of 120,000 to 140,000 daltons, is first treated with collagenase, which reduces its molecular weight by about 10,000 daltons. The treated protein is then digested with trypsin, and the digested protein subjected to gel filtration dialysis to isolate decapeptides of the general formula

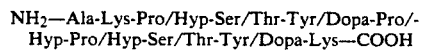

NH₂—Ala-Lys-Pro/Hyp-Ser/Thr-Tyr/Dopa-Pro/-Hyp-Pro/Hyp-Ser/Thr-Tyr/Dopa-Lys—COOH

The decapeptides produced in this manner are then polymerized by the use of chemical linking groups such as glutaraldehyde, oligopeptides, amino acids or other bifunctional linking groups to produce bioadhesives containing up to about 1,000 such decapeptide units.

The procedure of U.S. Pat. No. 4,585,585 still requires the isolation of bioadhesive protein from mussels, which, as previously indicated, is impractical on a commercial scale. Moreover, in addition to the laborious purification procedure, this process adds the additional steps of enzymatic digestion, isolation of the decapeptide fragments and chemical reassemblage of the fragments into a bioadhesive polymer. This arduous procedure is not well-suited to commercial production.

Thus, a need has continued to exist for means and methods for the efficient production of bioadhesives containing the decapeptide units.

A further need has continued to exist for means and methods for producing bioadhesives containing the decapeptide units without the necessity of handling and processing large quantities of mussels.

SUMMARY OF THE INVENTION

This invention involves the production, in *Escherichia coli*, of bioadhesive precursor proteins which are analogous to the non-hydroxylated polyphenolic adhesive protein produced by *M. edulis*. The invention includes the vectors comprising the DNA sequences encoding the bioadhesive precursor protein analogs, *E. coli* hosts transformed with said vectors, the bioadhesive precursor proteins, and methods of producing the precursor protein.

The bioadhesive precursor protein which is produced by the process of the invention is comprised of three, five, ten, fifteen or twenty repeating decapeptides of the sequence Ala-Lys-Pro-Ser-Tyr-Pro-Pro-Thr-Tyr-Lys. For the proteins larger than five repeating decapeptides, a tripeptide linking group is present between the groups of five repeating decapeptides.

The protein produced by the process of the invention can be employed as a bioadhesive precursor. The adhesive properties of the protein are enhanced by hydroxylating at least a portion of the tyrosine residues to 3,4-dihydroxyphenylalanine (DOPA). The hydroxylated protein is cured to produce the desired physical properties in the bioadhesive.

The bioadhesive precursor protein analog is produced by the insertion into an *E. coli* host, of a replicable expression vector containing a chemically synthesized double-stranded DNA (dsDNA) sequence coding for the desired protein and expression of the synthetic dsDNA sequence in the host *E. coli* to yield the protein.

The dsDNA sequence encoding the bioadhesive precursor protein is linked, at its 5' end, to a 5' fragment of the *E. coli* trpB gene in order to facilitate transcription initiated at a host promoter. Additionally, the dsDNA sequence is linked at the 3' end to a 3' fragment of the calf chymosin gene. The expressed protein thus constitutes a tribrid fusion of the bioadhesive precursor protein, the chymosin fragment, and the trpB protein fragment. Insertion, between the sequences encoding the bioadhesive precursor protein and both the trpB protein fragment and the chymosin fragment, of a dsDNA sequence encoding the amino acid methionine, which is specifically cleavable by treatment with cyanogen bromide, provides a means of cleavage to separate the bioadhesive precursor protein from the trpB protein and chymosin fragments.

BRIEF DESCRIPTION OF THE DRAWINGS

FIG. 4 represents the DNA sequence and amino acid sequence of the portion of the tribrid gene of pGX2354 which codes for a 10 repeat decapeptide.

FIG. 5 represents the amino acid sequence of the bioadhesive precursor protein analog encoded by pGX2365, after cyanogen bromide cleavage.

DETAILED DESCRIPTION OF THE INVENTION

Figure 1:
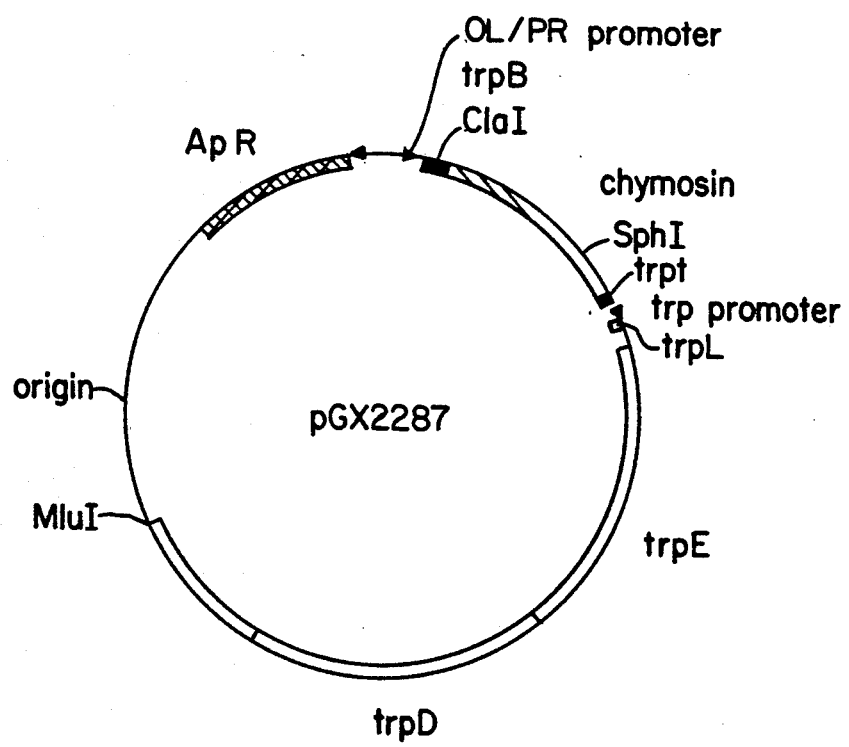
FIG. 1 is a diagram of *E. coli* plasmid pGX2287, containing the $O_L/P_R$ promoter and encoding a trpB-chymosin fusion protein.

The bioadhesive precursor protein produced by the process of the invention comprises three, five, ten, fifteen or twenty repeating decapeptides of the amino acid sequence Ala-Lys-Pro-Ser-Tyr-Pro-Pro-Thr-Tyr-Lys. Those proteins with ten, fifteen or twenty repeating decapeptides have the tripeptide Thr-Pro-Ala between each group of five repeating decapeptides.

The bioadhesive precursor protein analog is produced by inserting a synthetic dsDNA sequence encoding the protein into a replicable expression vector in which it is operably linked to a regulatory sequence that is capable of directing expression of the encoded protein in *E. coli* cells. Such *E. coli* cells can then be transformed with the expression vector, grown up and subjected to conditions under which the protein is expressed. For purposes of this invention, the term "recombinant protein" is intended to mean a protein produced by *E. coli* cells transformed with such a recombinant replicable expression vector.

The dsDNA sequence encoding the bioadhesive precursor protein may be prepared by any of the known methods of DNA synthesis. A suitable method for synthesizing the dsDNA sequence is the phosphite solid-phase method (Tetrahedron Letters, 21:719–722 (1980)). The dsDNA is characterized by the fact that it codes for a protein which is an analog of the naturally occurring *M. edulis* adhesive protein. By the term "analog" is intended a protein which differs from the naturally occurring protein in its exact amino acid sequence but which includes decapeptide repeating units which are common to the non-posttranslationally modified naturally occurring *M. edulis* adhesive protein. By the term "bio-adhesive precursor protein analog" is intended proteins produced in genetically engineered *E. coli* which comprise three, five, ten, fifteen or twenty repeating decapeptide units of the sequence Ala-Lys-Pro-Ser-Tyr-Pro-Pro-Thr-Tyr-Lys.

Two basic approaches to synthesize, clone, and express dsDNA sequences encoding a bioadhesive precursor protein analog containing three, five, ten, fifteen, or twenty repeats of the decapeptide sequence described above were evaluated. The first approach was to:

(a) synthesize oligonucleotides encoding one decapeptide;

(b) ligate the oligonucleotides to assemble decapeptide multimer coding sequences;

(c) clone the multimer coding sequences in *E. coli* cloning vectors, using specifically designed linkers to facilitate insertion of the cloned oligonucleotides into the vectors; and (d) transfer the longest cloned sequences into *E. coli* expression vectors so that the sequences are expressed as fusion proteins.

This approach was used to assemble synthetic DNA sequences encoding the polypeptide (Ala-Lys-Pro-Ser-Tyr-Pro-Pro-Thr-Tyr-Lys)$_N$ where N indicates the number of direct repeats of this decapeptide sequence. This decapeptide is a non-hydroxylated component of the polyphenolic adhesive protein of *M. edulis* and was identified from tryptic digests of the natural protein (U.S. Pat. No. 4,585,585).

The inventors anticipated that a cloned multimer coding sequence containing 20 repeats of this 10-codon sequence might be unstable in *E. coli*. In order to limit the number of direct DNA repeats in the *E. coli* plasmids, five different oligonucleotides were synthesized, using different codon combinations. However, use of one particular oligonucleotide (GCG AAA CCA AGT TAC CCA CCG ACC TAC AAA) encoding the above referenced decapeptide resulted in the most efficient assembly of the multimer coding sequence, and the resulting repetitive DNA sequence was found to be stable in *E. coli*.

DNA sequencing and/or restriction enzyme analysis of clones obtained by this approach indicated that DNA fragments encoding up to nine decapeptide repeats had been cloned in *E. coli*. However, many of the clones had errors in the DNA sequences, causing incorrect codons, frame shifts or termination codons. Therefore, an improved approach for generating the homogeneous 20-decapeptide repeat coding sequence was developed.

The second approach, represented in Example 1, was to:

(a) synthesize oligonucleotides encoding one decapeptide;

(b) ligate the oligonucleotides to assemble decapeptide multimer coding sequences;

(c) clone the multimer coding sequences in *E. coli* expression vectors, using specifically designed 5' and 3' linkers to facilitate insertion of the oligonucleotides and to provide unique restriction sites at the ends of the cloned sequence; and (d) expand the cloned decapeptide coding sequence repeats in the *E. coli* expression vectors using the unique restriction sites at the 5' and 3' ends.

The resulting synthetic dsDNA encoding the bioadhesive precursor protein analog is inserted into the *E. coli* expression vector under the control of a regulatory sequence containing a promoter, ribosome binding site and translation initiation signal capable of effecting expression in the *E. coli* host.

In order to limit the problem of sequence deletion caused by homologous recombination in *E. coli*, the recA *E. coli* host GX3015 was utilized. The synthetic DNA was cloned directly into a derivative of an expression vector (pGX2287, see FIG. 1) previously developed for the production of bovine chymosin (fully described in U.S. Pat. No. 4,798,791 and deposited with the USDA Northern Regional Research Laboratory, Peoria, Ill. with accession No. NRRL-B15788) such that tribrid fusion genes were produced. The genes contain a 5' segment of the highly expressed trpB gene to promote efficient translation initiation, followed by the synthetic bioadhesive precursor protein analog gene, and a 3' region encoding the 159 carboxy terminal amino acids of bovine chymosin. Methionine codons are located on either end of the bioadhesive precursor protein segment so that cyanogen bromide cleavage can be used to release the bioadhesive precursor protein analog from the tribrid fusion protein. As those skilled in the art are aware, cyanogen bromide cleaves proteins at methionine residues. Since there are no internal methionine residues within the bioadhesive precursor protein itself, this protein remains intact. Additionally, the plasmid contains a synthetic trot sequence 3' of the gene to stabilize the mRNA and the trpED genes that effectively stabilize the plasmids in the GX3015 deltatrpED102 host when growth medium without tryptophan is utilized. The promoter is a hybrid lambda OL/PR promoter (fully described in commonly assigned U.S. patent application No. 07/237,616, now abandoned that is regulated by the temperature-sensitive cI857 repressor produced by a defective lambda lysogen in the GX3015 host.

Figure 2:
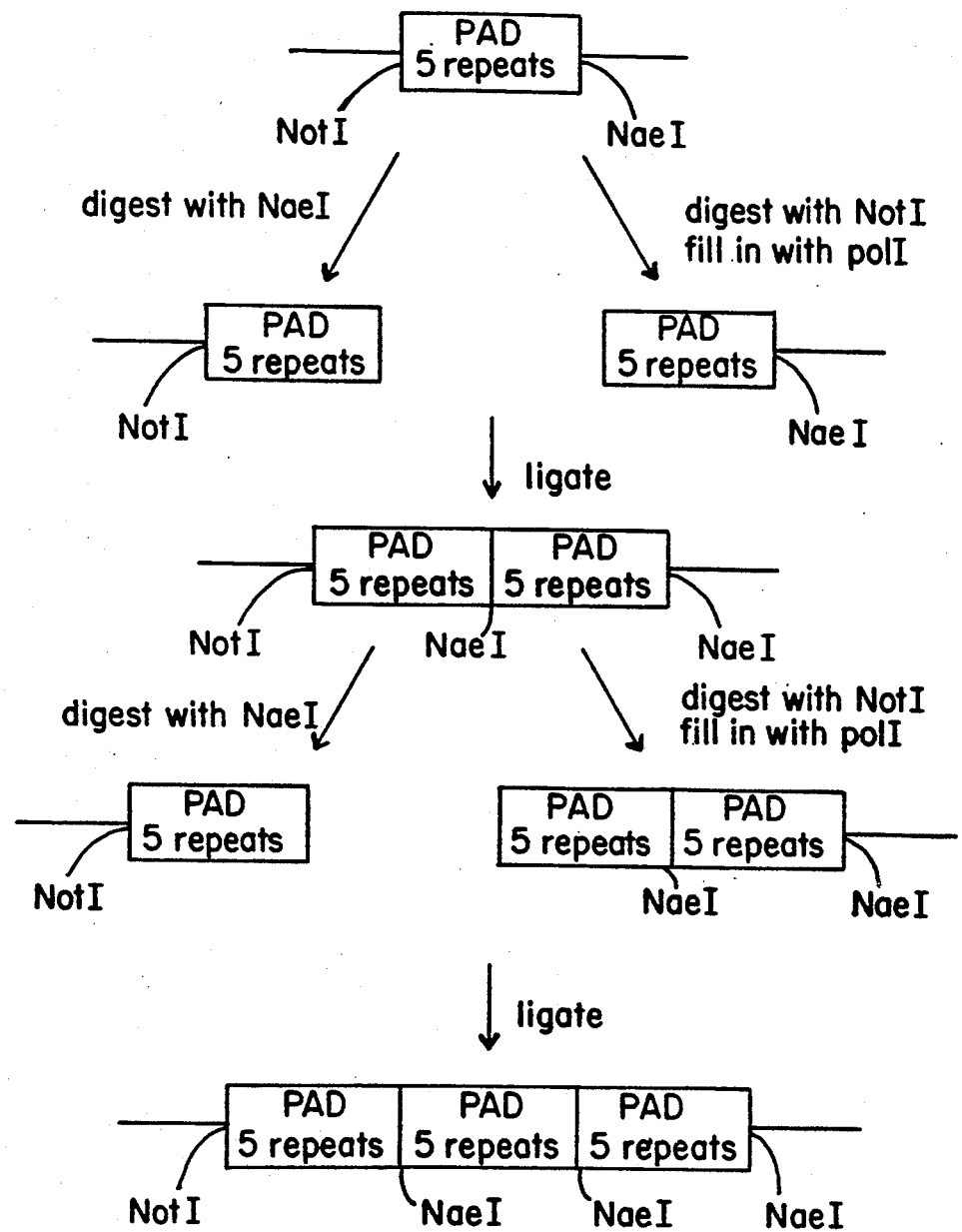
FIG. 2 is a flow chart describing the assembly of a repetitive DNA sequence encoding a bioadhesive precursor protein analog PAD=polyphenolic adhesive decapeptide.

To assemble DNA sequences encoding repeats of the decapeptide Ala-Lys-Pro-Ser-Tyr-Pro-Pro-Thr-Tyr-Lys, oligonucleotides were synthesized that encode the decapeptide sequence and 5' and 3' linker sequences that provide unique restriction sites. These oligonucleotides were annealed and ligated with an *E. coli* expression vector to generate pGX2346, a plasmid that contains three decapeptide coding repeats. The 5' linker encodes a NotI site and the 3' linker encodes a NaeI site. The 5'-end of the pGX2346 decapeptide coding sequence generated by NotI digestion and treatment with DNA polymerase I to fill in the overhang was ligated to the blunt 3-end of the decapeptide coding sequence generated by digesting a second aliquot of pGX2346 with NaeI (see FIG. 2). This creates an in-frame fusion through a linker region that codes for Thr-Pro-Ala. The 5', 3' and internal linkers all code for amino acids (ala, thr, pro, ser) that are found in the prototype decapeptide and thus do not disrupt the general characteristics of the translation products. NotI and NaeI sites were chosen for the linkers because they are unique sites in the plasmids and therefore, simplify the ligations to increase the synthetic gene length. For example, a plasmid with a five decapeptide repeat gene (pGX2348) was doubled to a ten repeat gene (pGX2354) with the thr-pro-ala linker between two five decapeptide repeat genes by simply ligating NotI/DNA polymerase I treated pGX2348 DNA with another aliquot of pGX2348 DNA digested with NaeI, followed by digestion with PvuI (a site in the bla gene of pGX2348) and ligation again at low DNA concentration to favor recircularization of the plasmid. Using this method of multiplying the repeats by ligating NotI/DNA polymerase I treated plasmid DNA to another sample of plasmid cut with NaeI, synthetic genes encoding fifteen (pGX2358) and twenty (pGX2365) repeats were also constructed.

The expression vector containing the inserted dsDNA coding for the bioadhesive precursor protein analog is used to transform *E. coli* by known techniques of transformation. The transformed *E. coli* cells are cultured under conditions suitable for growth and expression of the bioadhesive precursor protein analog gene. After the protein has been expressed, it is recovered from the transformant cells by known methods such as mechanical or chemical lysis of the cells. The protein can be purified using procedures known in the art, including well-known chromatographic procedures. The bioadhesive precursor protein analog is preferably purified to homogeneity or near homogeneity. In the case of a fusion protein, the recovered protein can be subjected to cyanogen bromide cleavage to remove extraneous peptide sequences.

In the following example, the method employed for the synthesis of oligodeoxyribonucleotides is the methyl-phosphite solid-phase method (Matteucci, M. D. and Caruthers, M. H., *Tetrahedron Letters*, 21:719–722 [1980]) using an automated solid-phase DNA synthesizer manufactured by Applied Biosystems, Inc. The starting materials, such as the four appropriately protected 5'-dimethoxytrityl-2'-deoxyribonucleoside-3'-phosphoramidites as well as the solid support such as silica and controlled pore glass (CPG) (Adams, S. P., Kavka, K. S., Wykes, E. J., Holder, S. B. and Gallappi, G. R., *J. Amer. Chem. Soc.*, 105:661–663 [1983]) derivatized with appropriately protected 5'-dimethoxytrityl-2'-deoxyribonucleosides, are commercially available.

The DNA synthesis proceeds from the 3'-end to the 5'-end. For the synthesis of, for example, the single strand

5' GCG AAA CCA AGT TAC CCA CCG ACC
TAC AAA 3' the derivatized solid support containing approximately 1 umol of protected 5'-dimethoxytrityl-2'-deoxyadenosine is loaded in a synthesis column and placed into the automated DNA synthesizer. The coupling cycle consists of detritylation of the solid support with 2% trichloroacetic acid in dichloromethane; washing with anhydrous acetonitrile; simultaneous addition of an appropriately protected 5'-dimethoxytrityl-2'-deoxyribonucleoside-3'-phosphoramidate (10 umol) in acetonitrile and tetrazole (30 umol) in acetonitrile, incubation for one minute, capping of unreacted 5'-hydroxyl groups with acetic anhydride and dimethyl-aminopyridine in tetrahydrofuran; oxidation with iodine in a mixture of tetrahydrofuran, lutidine and water [2:1:2]; and final washing with anhydrous acetonitrile. The coupling cycle is repeated until the desired length of DNA is obtained. The DNA is then partially deprotected by treatment with thiophenoxide in dioxane/triethylamine and it is released from the solid support by several (2-4) brief treatments (5-10 minutes) with concentrated ammonium hydroxide. Completely deprotected DNA is obtained by heating the concentrated ammonium hydroxide solution at 60-65 degrees C. for 8-14 hours.

The DNA is then purified by ion-exchange and linear preparative polyacrylamide gel electrophoresis. The purified DNA is enzymatically phosphorylated at the 5'- end and characterized prior to subsequent ligation.

EXAMPLE 1

Production of Antibody to Bioadhesive Precursor Protein Analogs

Synthetic decapeptide (1.5 mg) of the sequence Ala-Lys-Pro-Ser-Tyr-Pro-Pro-Thr-Tyr-Lys, prepared by the Merrifield solid-state method, was combined with 2.0 mg of bovine serum albumin (BSA) in 1.8 ml phosphate-buffered saline. One percent glutaraldehyde (0.2 ml) was added and the solution was incubated 30 minutes at 22° C. Sodium borohydride was added to a final concentration of 0.5 mg/ml and incubation was continued at 22° C. for one hour. The solution was then dialyzed against phosphate-buffered saline. Amino acid analysis of the resulting protein indicated 35 moles of peptide were coupled per mole of BSA.

Rabbits were given intramuscular injections with 100 ug of peptide (BSA coupled) in incomplete Freund's adjuvant. Booster subcutaneous injections using incomplete Freund's adjuvant were given subsequently in two-week intervals. Antiserum with high-titer antibody reactive toward the decapeptide as well as M. edulis bioadhesive precursor protein isolated from mussels or analog proteins produced in microorganisms was obtained by this method.

EXAMPLE 2

Figure 3:
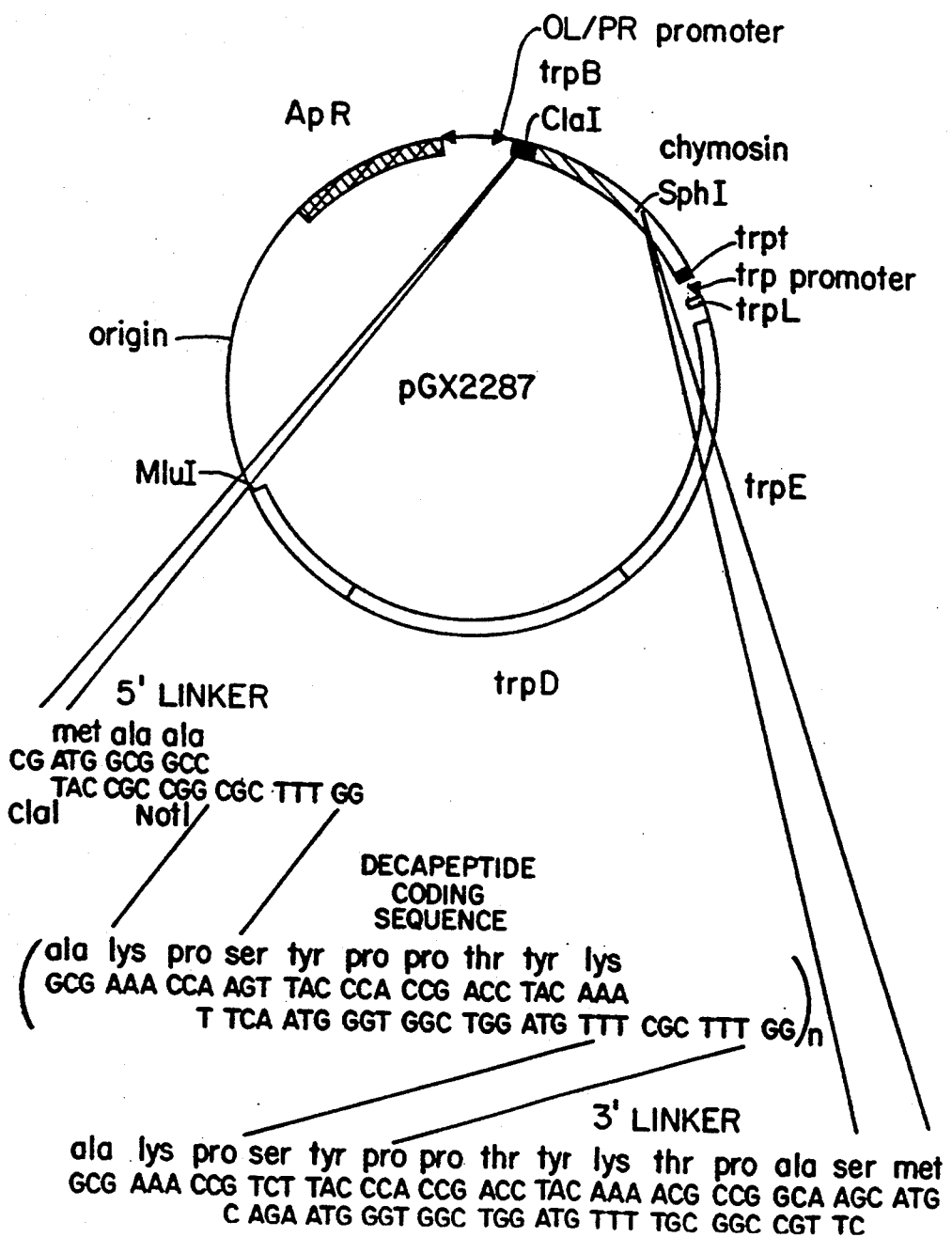
FIG. 3 depicts a method of inserting synthetic DNA sequences encoding bioadhesive precursor protein analogs into *E. coli* plasmid pGX2287 to generate coding sequences for a tribrid fusion protein.

Synthesis, Cloning and Expression in E. coli of Sequences Encoding a Bioadhesive Precursor Protein Analog Containing from 3 to 20 Repeats of the Ala-Lys-Pro-Ser-Tyr-Pro-Pro-Thr-Tyr-Lys Decapeptide A. Assembly of pGX2346. Plasmid pGX2287 (NRRL-B15788), part of a vector/host system for expression of bovine chymosin, was used as the E. coli cloning and expression vector for bioadhesive precursor protein analog coding sequences. FIG. 3 outlines the DNA pieces that were assembled during initial cloning experiments. Synthetic DNA coding for one decapeptide flanked by 5' and 3' linkers was cloned between unique ClaI and SphI endonuclease sites of pGX2287 such that a synthetic tribrid gene was formed, containing a 5' segment of the efficiently expressed trpB gene, the bioadhesive precursor protein analog coding sequence and a 3' region encoding 159 carboxy terminal amino acids of bovine chymosin. This tribrid gene was utilized because the 5' trpB portion provides efficient transcription and translation initiation and the chymosin portion results in accumulation of the fusion protein as inclusion bodies. Inclusion body formation can lend stability to a foreign protein and provide a convenient method of initial purification. Methionine codons were situated on either side of the bioadhesive precursor protein analog coding sequence, so that the bioadhesive precursor protein can be easily excised from the resulting fusion protein by treatment with cyanogen bromide.

The synthetic DNA shown in FIG. 3 was synthesized as seven oligonucleotides using an Applied Biosystems DNA synthesizer (phosphoramidite chemistry). These oligonucleotides were designated:

| Oligonucleotide Number | Sequence | Function |
| --- | --- | --- |
| 1875 | GGTTTCGCGGCCGCCAT | 5' linker |
| 1876 | CGATGGCGGCC | 5' linker |
| 1877 | CTTGCCGGCGTTTTGTAGGTCGGTGGGTAAGAC | 3' linker |
| 1892 | GCGAAACCGTCTTACCCACCGACCT | 3' linker |
| 1893 | ACAAAACGCCGGCAAGCATG | 3' linker |
| 1545 | GCGAAACCAAGTTACCCACCGACCTACAAA | decapeptide sequence |
| 1546 | GGTTTCGCTTTGTAGGTCGGTGGGTAACTT | decapeptide sequence |

After purification by preparative gel electrophoresis and reverse-phase chromatography, the oligonucleotides were dissolved at a concentration of 1.0 delta 280 unit/ml. Oligonucleotides #1876, #1877, and #1892 were phosphorylated individually in reactions with T4 polynucleotide kinase and 1 mM ATP with 20 ul of oligonucleotide solution added in a 50 ul kinase reaction. Oligonucleotides #1545 and #1546 were similarly treated, except they were pooled first at a 1:1 ratio. After the enzyme reaction, the solutions were boiled for two minutes to inactivate the enzyme. An equivalent amount of oligonucleotide #1875 was added to the #1876 kinase reaction, boiled for 30 seconds, then allowed to slow cool for formation of 5' linker. Likewise, the #1892 and #1877 kinase reactions were mixed together with an equivalent amount of non-kinased #1893' boiled, slow cooled and then ligated in a 180 ul volume at 16° C. for 11 hours with T4 polynucleotide ligase to assemble the 3' linker.

Plasmid pGX2287 DNA (5 ug) was digested with 18 units of ClaI endonuclease then extracted with phenolchloroform, ethanol precipitated and dissolved in 0.01M Tris-HCl, 0.001M EDTA (pH 8.0) at 0.25 ug DNA/ul. Ten microliters of the ClaI-cut pGX2287 DNA was ligated with 25 ul of the 5' linker in a total volume of 40 ul at 16° C. for 11 hours. After ligation, the DNA was phenol-chloroform extracted, ethanol precipitated, then dissolved in 1 ml water. The DNA solution was concentrated using a Centricon 30 (Amicon) ultrafiltration unit, then washed two times with 2 ml water and centrifuged at 5,000 RPM for ten minutes. The washed and concentrated DNA, largely free of non-ligated linkers, was ethanol precipitated and dissolved in 10 microliters of water.

Three micrograms of the above ClaI-cut pGX2287 DNA with attached 5' linker was ligated in a 20 ul volume with 10 ul of the solution of kinased decapeptide coding DNA segments (oligonucleotides #1545 and #1546) at 22° C. After 40 minutes, 20 ul of the 3' linker ligation mixture (#1877, #1892, and #1893) was added and the ligation was continued for 12 hours at 22° C.

The ligation mixture was diluted to 150 ul in SphI endonuclease buffer and digested with SphI. Ten micrograms of tRNA was added, the solution was phenol-chloroform extracted, then ethanol precipitated. The DNA was finally dissolved and diluted to 200 ul in T4 ligase buffer and ligated at 15° C. overnight. The ligation was used to transform *E. coli* GX3015 (F− trpED102 tna2 recA nadA [chlD-pg1][lambda cI857 BamH1]) using standard procedures. Any other *E. coli* host is suitable that has recA, trpED mutations, and has a defective lambda lysogen with the lambda cI857 repressor. Cells were grown at 30° C. on LB+100 ug/ml ampicillin or minimal medium containing 0.4% glucose, 0.4% acid hydrolyzed casein (casamino acids, Difco), and 100 ug/ml ampicillin. One characterized transformant, upon heating to 37° C., produced a protein that reacted with both anti-chymosin antibody and anti-decapeptide antibody (produced in accordance with Example 1) in Western blot experiments (Burnette, W. N., 1981, *Anal. Biochem.*, 112:195–203). The plasmid in this transformant was named pGX2346 and DNA sequence analysis demonstrated that the synthetic gene contained a 5' and 3' linker with two internal decapeptide coding segments for a total of three decapeptide coding segments (one of these decapeptides is encoded by the 3' linker, see FIG. 3).

B. Increasing the size of the bioadhesive precursor protein analog coding sequence to construct pGX2348. The 5' and 3' linkers flanking the three decapeptide coding sequence in pGX2346 were designed with unique restriction sites such that the size of the bioadhesive precursor protein analog coding sequence could be increased through a simple ligation procedure without requiring further oligonucleotide ligations. The 5' linker contains a NotI site and the 3' linker contains a NaeI site. The 5'-end of the three decapeptide coding sequence generated by NotI digestion of pGX2346 followed by treatment with DNA polymerase I was ligated to the blunt 3'-end of the three decapeptide coding sequence generated by NaeI digestion of second aliquot of pGX2346 (see FIG. 2). This creates an in-frame fusion through a linker region that codes for thr-pro-ala. The 5', 3' and internal linkers all code for amino acids (ala, thr, pro, ser) that are used in the prototype decapeptide and thus do not disrupt the general characteristics of the translation products.

About 0.5 ug of pGX2346 DNA was cut with NotI in a volume of 20 ul. A second 0.5 ug aliquot of pGX2346 DNA was cut with NaeI. The DNA solutions were extracted with phenolchloroform, ethanol precipitated and dissolved in 20 ul of water. The NotI-digested DNA was reacted with T4 DNA polymerase in a 100-ul reaction with 0.25 mM dATP, dGTP, dCTP, dTTP at 37° C. for 30 minutes to fill in the NotI-generated single-stranded end. The DNA was extracted, precipitated and dissolved in water. About half of the NotI/PolI treated DNA and half of the NaeI-treated DNA were ligated together in a 20-ul volume at 22° C. for 4.5 hours with T4 polynucleotide ligase and 0.5 mM ATP. The ligation was diluted to 100 ul with PvuI buffer and digested with 28 units of PvuI for one hour at 37° C. Carrier tRNA (20 ug) was added, and the reaction was extracted and precipitated. Finally, the DNA was ligated at 15° C. for 8 hours in a volume of 150 ul to promote circular DNA formation at low DNA concentration. GX3015 cells were transformed with the ligation mixture.

One transformant that was characterized had a plasmid shown by DNA sequencing to encode a bioadhesive precursor protein analog of five decapeptide repeats instead of the expected six repeats. Also the thr-pro-ala coding sequence expected to result from joining 5' and 3' linkers was not present. The likely explanation for this observation is that one decapeptide coding repeat and the linker were lost in a homologous recombination event. The new plasmid was designated pGX2348. When cells containing pGX2348 are grown at 30° C., then shifted to 37° C., they produce a 27,000 molecular weight protein that reacts with anti-decapeptide antibody, as expected.

C. Further expansion of the bioadhesive precursor protein analog coding sequence. Plasmid pGX2348 with a five-decapeptide coding sequence was taken through the same ligation procedure described for pGX2346 above, resulting in a transformant containing plasmid pGX2354, with exactly the predicted structure (see FIG. 4). There are two segments that each code for five tandem decapeptide repeats separated by a thr-pro-ala tripeptide coding sequence. The joining of the 5' and 3' linkers at the NotI and NaeI sites regenerates the NaeI site. Therefore, further use of the ligation procedure described above resulted in size increases in increments of five-decapeptide coding repeats. Thus, pGX2354 (10-decapeptide repeats) was used for the construction of pGX2358 (15-decapeptide repeats) and pGX2358 was used for the construction of pGX2365 (20-decapeptide repeats). Although the DNA sequence of the inserts in pGX2358 and pGX2365 were not determined, they have internal NaeI sites and also produce immunoreactive proteins of the expected molecular weights before and after cyanogen bromide cleavage, as shown below. These data are consistent with synthetic genes of the expected structure, i.e., tandem decapeptide coding repeats separated by a tripeptide coding segment.

| Plasmid | Number Decapeptide Repeats | Precursor Protein Analog M.W. | CNBr-Cleaved Precursor Analog M.W. |
| --- | --- | --- | --- |
| pGX2346 | 3 | 24,729 | 4,004 |
| pGX2348 | 5 | 26,996 | 6,270 |
| pGX2354 | 10 | 32,931 | 12,206 |
| pGX2358 | 15 | 38,854 | 18,128 |

| Plasmid | Number Decapeptide Repeats | Precursor Protein Analog M.W. | CNBr-Cleaved Precursor Analog M.W. |
|---|---|---|---|
| pGX2365 | 20 | 44,803 | 24,077 |

FIG. 5 shows the amino acid sequence of the 24,077 molecular weight bioadhesive precursor protein analog produced by cells containing plasmid pGX2365 after cyanogen bromide cleavage.

D. Analysis of the Decreased Bioadhesive Precursor Protein Analog Accumulation with Increasing Decapeptide Repeat Length. Based on the intensity of immunological reaction in Western blots (FIG. 6), and Coomassie-stained total cellular protein (data not shown), the *E. coli* cells with plasmids pGX2346 and pGX2348 produced the bioadhesive precursor protein as several percent of the total insoluble protein, but as the number of decapeptide repeats was increased to 10, 15 and 20, significantly less protein was produced. That is, the gene expression level was inversely dependent on the number of encoded decapeptide repeat units. The plasmid series pGX2346 through pGX2365 with three to twenty repeats were constructed to be identical, except for the length of the synthetic bioadhesive precursor protein gene. Therefore, it seems likely that the decreased expression level is associated directly with the increased size of the expressed gene.

E. Fermentation of *E. coli* strains for production of the bioadhesive precursor protein analog. Plasmid pGX2287 contains the bla gene which encodes beta-lactamase, providing ampicillin resistance, as well as the trpED genes that in trytophan-deficient medium complement the trpED102 deletion in the host GX3015 chromosome. Transformed cultures of *E. coli* GX3015 were grown with 100 ug/ml ampicillin and/or in medium lacking tryptophan.

A single colony of GX3015 containing one of the plasmids described in Section C above is picked after growth on minimal salts medium (Miller, J. H., "Experiments in Molecular Genetics," Cold Spring Harbor Laboratory, 1972, p.432) supplemented with 0.4% casamino acids and 0.4% glucose and inoculated into 5 ml of LB medium supplemented with 100 ug/ml ampicillin. After reaching an optical density (A600) of greater than 1.0, 0.4 ml of the culture is inoculated into each of two 250-ml baffled flasks containing 50 ml of LB broth supplemented with 100 ug/ml ampicillin. The two flasks are incubated at 30° C. and shaken at 250 RPM for 6.5 to 9 hours.

Fermentation is carried out using eight liters of the following initial medium:

| | |
|---|---|
| $(NH_4)_2SO_4$ | 30 g |
| $KH_2PO_4$ | 15 g |
| $K_2HPO_4$ | 5 g |
| Biotin (0.5 mg/ml in 95% ethanol) | 12 ml |

Add tap water to eight liters, autoclave.

The following additions are made after autoclaving to provide the initial medium:

| | | |
|---|---|---|
| $CaCl_2\ 2H_2O$ | 10 ml of 10% | (w/v) sterile solution |
| glucose | 360 ml of 50% | (w/v) sterile solution |

| | | |
|---|---|---|
| niacin | 18 ml of 0.5% | (w/v) sterile solution |
| Trace solution 1 | 90 ml | |
| Trace solution 2 | 18 ml | |
| Trace solution 3 | 1.8 ml | |

The following fermentation conditions are maintained:

| | |
|---|---|
| pH 7.0 (controlled by 5N $NH_4OH$, and 1N $H_3PO_4$) | |
| Sparge rate | 1 vvm |
| Temperature | 32° C. |
| Agitation rate | 800 r.p.m. |

In order to increase cell density prior to induction of expression, a system of broth supplementation with nutrients is undertaken. The feed solution is prepared as follows:

A solution of 1,000 g glucose in deionized water (final volume of 1700 ml) is autoclaved. After autoclaving, trace mineral solutions are added:

| | |
|---|---|
| Trace Solution 1 | 500 ml |
| Trace Solution 2 | 100 ml |
| Trace Solution 3 | 10 ml |
| $CaCl_2.2H_2O$ | 50 ml |
| Trace Solution 1 | |
| $H_2O$ | 900 ml |
| conc HCl | 13.1 ml |
| $FeCl_2.6H_2O$ | 5.4 g |
| $ZnSO_4.7H_2O$ | 1.44 g |
| $MnCl_2.4H_2O$ | 1.0 g |
| $CuSO_4.5H_2O$ | 0.25 g |
| $CoCl_2.6H_2O$ | 0.24 g |
| $H_3BO_3$ | 0.062 g |

Brought to 1000 ml and sterile filtered.

| | |
|---|---|
| Trace Solution 2 | |
| $H_2$ | 900 ml |
| HCl | 44.8 ml |
| $MgSO_4.7H_2O$ | 61.6 g |
| Brought to 1000 ml and sterile filtered. | |
| Trace Solution 3 | |
| $H_2O$ | 1000 ml |
| $Na_2MoO_4.2H_2O$ | 24.1 g |
| Sterile filtered. | |

The feed solution is initially added to the broth in a volume of 180 ml and thereafter as needed to maintain the glucose level at 10 g/liter. Feed supplementation is continued until the A600 reaches 20, at which time the cells are induced to express the tribrid bioadhesive precursor protein gene from the hybrid lambda $O_L/P_R$ promoter. Induction is effected by raising the temperature to 42° C. for one hour to deactivate the temperature-sensitive lambda cI857 repressor protein produced by the defective lambda lysogen in the GX3015 chromosome. The fermentation is continued at 37° C. for another 6–8 hours.

EXAMPLE 3

Experiments to Improve the Expression of the Bioadhesive Precursor Protein Analog Containing Twenty Repeats of the Decapeptide (Ala-Lys-Pro-Ser-Tyr-Pro-Pro-Thr-Tyr-Lys)

Plasmid pGX2365 was further manipulated in attempts to increase expression of the 20-repeat protein in *E. coli*. In particular to examine the effect of chymosin sequences on expression level and intracellular solubility, two new variants of pGX2365 were prepared as described below.

Plasmid pGX2365 has a unique SphI site at the end of the decapeptide multimer coding sequence, a unique BanII site within the chymosin coding sequence and a unique BclI site at the end of the chymosin coding sequence. Oligonucleotides were synthesized and annealed to yield the linker shown below that could be used for stepwise deletion of chymosin sequences from the gene.

| C AGC ATG CCA GGC CTG T |
| --- |
| CC GGG TCG TAC GGT CCG GAC ACT AG |
| BanII    SphI              BclI |
| Pro Ser Met Pro Gly Leu * |

The linker was first inserted between the BanII and BclI sites of pGX2365 to create pGX2374. The protein produced from pGX2374 has only 61 carboxy-terminal amino acids derived from chymosin plus four linker amino acids. The deletion removed the 98 carboxy-terminal chymosin amino acids, including two of the four cysteines originally present in the chymosin segment. Digestion of pGX2374 with SphI followed by removal of the small SphI fragment and recircularization resulted in deletion of the remaining chymosin sequences, leaving only the carboxy-terminal amino acids met-pro-gly-leu encoded by the linker sequence after the decapeptide repeats. This plasmid was designated pGX2375.

Figure 6:
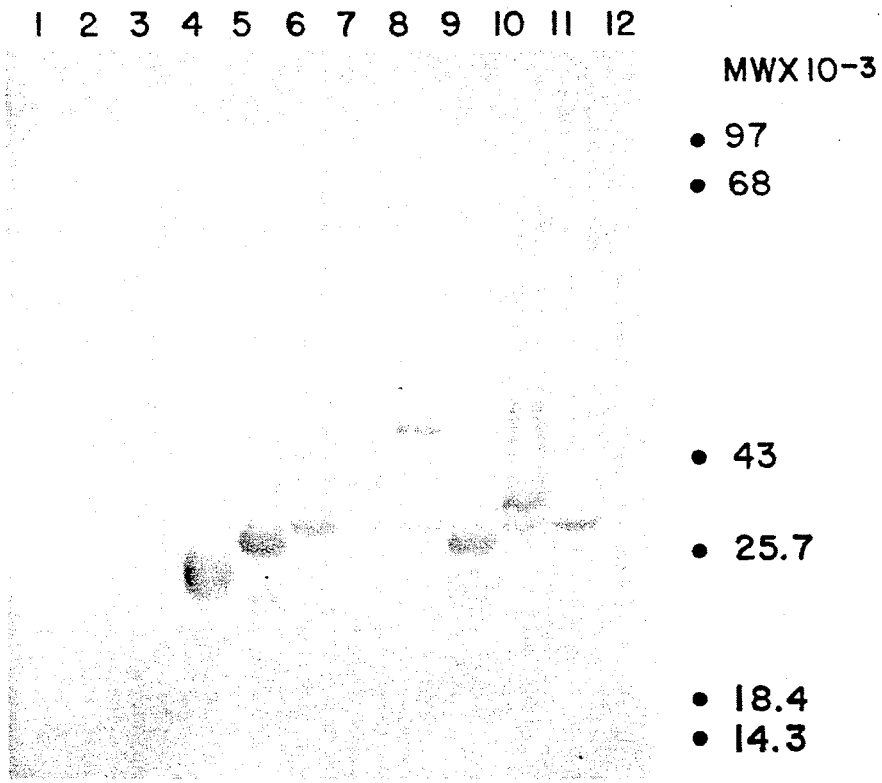
FIG. 6 represents a Western blot analysis for several bioadhesive precursor protein analogs produced in *E. coli*.

The expression level and solubility of decapeptide multimer protein produced with pGX2374 and pGX2375 was compared with all the earlier plasmids in the Western blots shown in FIG. 6.

EXAMPLE 4

Purification of Bioadhesive Precursor Protein Analogs

E. coli GX3015 cells containing one of the plasmids described in Example 2 (32 g wet weight) are suspended in 20 ml 20 mM Tris-HCl, 2 mM EDTA (pH 7.5), 1 mM phenylmethylsulfonyl fluoride, 25 mM iodoacetic acid, and thoroughly disrupted by passage through a French press followed by sonication. The cell debris and inclusion bodies containing bioadhesive precursor protein are pelleted by centrifugation at 27,500 g for 30 minutes at 4° C. The pellet is extensively washed by suspension in 10 mM Tris-HCl, 1 mM EDTA (pH 7.5) and centrifugation. Washing is continued until the supernatant is clear. The pellet is then dissolved in 15 ml of 6 M guanidine hydrochloride, 5% beta-mercaptoethanol, 25 mM iodoacetic acid, and centrifuged at 30,000 ×g for 30 minutes at 4° C. The supernatant is dialyzed against 4 liters of 0.2 mM EDTA, 10 mM iodoacetic acid, with 3 changes which results in protein precipitation. The precipitate containing about 0.5 g of protein is dissolved in 40 ml of 70% formic acid. Cyanogen bromide (1.3 g) is added and the solution is allowed to react overnight at room temperature. After rotary evaporation, the residue is extracted with 20 ml water (pH 4.0 from residual formic acid). The pH of the water-soluble fraction is adjusted to pH 7.0 with 5N KOH resulting in some precipitate formation. The supernatant is then applied to a CM cellulose or S-Sepharose column (2.5×26 cm) equilibrated with 50 mM potassium phosphate (pH 7.5). After the column is washed for 14 hours with 50 mM potassium phosphate, the bioadhesive precursor protein is eluted with either a salt gradient (0 to 0.5M KCl) or a pH change (pH 8 to pH 10) in the buffer. The fractions are assayed by measurement of absorbance at 280 nm and by SDS polyacrylamide gel electrophoresis using both Coomassie blue protein stain and the Western blot assay with specific antibodies (Example 1). The fractions containing the bioadhesive precursor protein analog are pooled and dialyzed overnight twice against 2 liters of deionized water. The resultant suspension is lyophilized and 1 mg of purified material is obtained. Material could be further purified, if necessary, using Sephadex G-75 column chromatography with 0.3M ammonium acetate pH 4.0. Bioadhesive precursor protein eluting in the first protein peak is dialyzed against water and lyophilized for recovery as a salt-free powder.

The purified protein is hydrolyzed in 6M constant boiling HCl with phenol crystals in vacuo at 105° C. for 24 hours. The amino acids in the acid hydrolysate are identified as O-phthaldehyde (OPA) derivatives which are separated on C18 reverse-phase HPLC column (Fleury, M. O. and D. V. Ashley, Anal. Biochem., 133:330–335 (1983)). The amino acid composition is used to verify purity since only a specific subset of amino acids is present in bioadhesive precursor protein.

What is claimed is:

1. An E. coli recombinant expression vector comprising plasmid pGX2287 and a DNA sequence of a bioadhesive precursor protein analog wherein said DNA sequence is selected from the group consisting of:
   a. $X_N$ where X=GCG AAA CCA AGT TAC CCA CCG ACC TAC AAA N=3 or 5 and G, A, T, and C represent the deoxyribonucleotides containing the bases guanine, adenine, thymine and cytosine, respectively;
   b. $X_5YX_5$ where X, G, A, T, and C are as defined above and Y=ACG CCG GCC;
   c. $X_5YX_5YX_5Y$ where X, Y, G, A, T, and C are as defined above; and
   d. $X_5YX_5YX_5YX_5Y$ where X, Y, G, A, T, and C are as defined above;

and wherein expression of said DNA sequence in said E. coli is under the control of said plasmid's $O_L/P_R$ promoter, and trpB ribosome binding site and translation initiation signal.

2. An E. coli cell comprising the recombinant vector of claim 1.

* * * * *